US009320574B2

(12) United States Patent
Nakagawa et al.

(10) Patent No.: US 9,320,574 B2
(45) Date of Patent: Apr. 26, 2016

(54) LIQUID TANK AND DENTAL DEVICE

(75) Inventors: Masaki Nakagawa, Tochigi (JP);
Shinichi Tanaka, Tochigi (JP);
Tomohiro Sakanushi, Tochigi (JP)

(73) Assignee: NAKANISHI INC., Tochigi (JP)

( * ) Notice: Subject to any disclaimer, the term of this patent is extended or adjusted under 35 U.S.C. 154(b) by 922 days.

(21) Appl. No.: 13/484,620

(22) Filed: May 31, 2012

(65) Prior Publication Data

US 2012/0305098 A1 Dec. 6, 2012

(30) Foreign Application Priority Data

Jun. 2, 2011 (JP) ................................. 2011-124114

(51) Int. Cl.
*A61C 1/00* (2006.01)
*A61C 17/20* (2006.01)

(52) U.S. Cl.
CPC ............. *A61C 1/0061* (2013.01); *A61C 1/0084* (2013.01); *A61C 17/20* (2013.01); *Y10T 137/3084* (2015.04)

(58) Field of Classification Search
CPC ..... A61C 1/0061; A61C 1/0084; A61C 17/20
USPC ................. 137/197, 587, 845, 855, 858, 846; 215/11.5, 261, 271
See application file for complete search history.

(56) References Cited

U.S. PATENT DOCUMENTS

| | | | |
|---|---|---|---|
| 4,685,577 A * | 8/1987 | Chen ............................ | 215/11.5 |
| 5,577,638 A | 11/1996 | Takagawa | |
| 6,755,650 B2 * | 6/2004 | Decosterd et al. .............. | 433/88 |
| 7,131,838 B2 * | 11/2006 | Suzuki ............................ | 433/88 |
| 2007/0102388 A1 * | 5/2007 | Lewis et al. ................... | 215/11.1 |
| 2012/0267334 A1 * | 10/2012 | Yamashita et al. ........... | 215/11.5 |
| 2014/0124469 A1 * | 5/2014 | Richard ........................ | 215/11.5 |

FOREIGN PATENT DOCUMENTS

| | | |
|---|---|---|
| EP | 1529496 A2 | 5/2005 |
| EP | 2103272 A1 | 9/2009 |
| JP | 2002-320628 A | 11/2002 |

(Continued)

OTHER PUBLICATIONS

European Search Report for counterpart application EP12170452; Aug. 31, 2012.

(Continued)

*Primary Examiner* — Craig Schneider
*Assistant Examiner* — Daphne M Barry
(74) *Attorney, Agent, or Firm* — Pearne & Gordon LLP

(57) ABSTRACT

A liquid tank capable of preventing a gas passage from being clogged and a dental device including this liquid tank are provided. A liquid tank having an accommodation space in which a liquid L to be supplied to outside is accommodated includes a tank body having a mouth part with an opening, a cap mounted on the mouth part to close the opening, a liquid passage through which the liquid L in the liquid tank flows toward outside, a gas passage having a gap between the mouth part and the cap and a path communicatively connecting to the gap and the accommodation space, a liquid flow valve provided on the liquid passage to allow or inhibit a flow of the liquid L to outside, and an aeration valve provided on the gas passage to compensate for a negative pressure occurring in the accommodation space.

9 Claims, 8 Drawing Sheets

(56) References Cited

FOREIGN PATENT DOCUMENTS

| | | |
|---|---|---|
| JP | 2005-137660 A | 6/2005 |
| JP | 2010-136774 A | 6/2010 |

OTHER PUBLICATIONS

Japanese Office action for Application No. 2011-124114; dated Jun. 7, 2013.

* cited by examiner

LIQUID TANK AND DENTAL DEVICE

BACKGROUND OF THE INVENTION

1. Field of the Invention

The present invention relates to a liquid tank for accommodating a liquid and a dental device connected to a dental handpiece to which the liquid in this liquid tank is supplied.

2. Description of the Related Art

Examples of a dental device including a liquid tank having accommodated therein a liquid such as a chemical agent for use in dental treatment, a placing part where this liquid tank is placed, and a mechanism for supplying the liquid in the liquid tank to a dental handpiece are disclosed in Japanese Patent Application Publication No. 2002-320628 and Japanese Patent Application Publication No. 2005-137660. The liquid tank has a liquid flow valve that opens a liquid passage when mounted on the dental device so that the liquid in the liquid tank passes therethrough and closes the liquid passage when removed from the dental device. The liquid tank also has an aeration valve for compensating for a negative pressure occurring in the liquid tank due to outflow of the liquid from the liquid tank via the liquid flow valve. The aeration valve is provided on a gas passage which communicatively connects the inside of the liquid tank and the outside of the liquid tank.

SUMMARY OF THE INVENTION

In the liquid tank described above, the gas passage has one end provided with an inlet for intake of gas (typically, air) from outside. This inlet has an opening having a relatively small diameter, and is exposed to outside.

In an environment where dental devices are used, even not a little amount of subtle dust occurring by cutting teeth is included. This dust is inevitably taken into the gas passage from the inlet together with air. If a dental device on which the liquid tank is mounted is continuously used, the gas passage and further the aeration valve may be clogged with the dust. To prevent clogging with dust, maintenance such as cleaning of the gas passage can be performed, which is cumbersome for dentists and may be neglected. For example, although it is possible to inhibit dust from entering the gas passage by providing a filter to the inlet, the filter may be clogged with dust, and therefore this is not a fundamental solution.

The present invention was made in view of these problems, and has an object of providing a liquid tank capable of preventing a gas passage from being clogged and a dental device including this liquid tank.

With this object, as a result of diligent studies by the inventors regarding a portion where a gas passage is provided, a new finding has been obtained such that a gap having air permeability is present between a mouth part of a liquid tank and a cap mounted on the mouth part and, when a negative pressure occurs in the liquid tank, air sufficient to compensate for the negative pressure can be taken into a container of the liquid tank.

A liquid tank of the present invention completed based on this finding is a liquid tank having an accommodation space for accommodating a liquid, including a tank body having a mouth part with an opening for inflow and outflow of the liquid and a cap mounted on the mouth part to close the opening.

This liquid tank includes a liquid passage through which the liquid in the liquid tank flows toward outside, a liquid flow valve provided on the liquid passage to allow or inhibit a flow of the liquid to outside, and an aeration valve provided on a gas passage to compensate for a negative pressure occurring in the accommodation space.

In this liquid tank, the gas passage has a first path and a second path. The first path is present between the mouth part and the cap, and communicatively connects to outside. The second path communicatively connects to the first path and the accommodation space.

In the liquid tank of the present invention, the first path communicatively connecting to outside is present between the mouth part and the cap. Normally, a space between the mouth part and the cap is not necessarily sealed entirely, but it can be recognized that a gap is inevitably present between the mouth part and the cap due to manufacturing tolerances or other factors. If this gap continues in a direction of a member axis of the mouth part and the cap, an air path is ensured between the mouth part and the cap. Moreover, it is understood that this gap occurs continuously or intermittently in a circumferential direction of the mouth part and the cap over a wide range.

Since the gap between the mouth part and the cap is subtle compared with an inlet of a conventional liquid tank, dust is difficult to enter the gap to begin with. Even if dust enters, the gap is present in the circumferential direction of the mouth part and the cap over a wide range, and thus only a part of the gap can be clogged with dust. Therefore, according to the liquid tank of the present invention, there is not a possibility that the gas passage is clogged with dust. In addition, if the cap is separated from the mouth part, wall surfaces of the mouth part and the cap configuring the first path are exposed, which can be cleaned at ease.

Furthermore, in the present invention, the gap between the mouth part and the cap is used as a first path. Therefore, at least a member for forming a gas passage corresponding to the first path is not required to be separately prepared, thereby contributing to low cost by reducing the number of components.

In the present invention, the second path is preferably at least partially formed in a sealing member sealing a space between the mouth part and the cap.

In the liquid tank, generally, in order to prevent the liquid accommodated in the accommodation space from leaking to the outside of the liquid tank, a sealing member is interposed between the mouth part and the cap. This sealing member faces the accommodation space and is in contact with the liquid accommodated therein. Therefore, if the second path is formed in the sealing member, it is possible to ensure the second path communicatively connecting to the first path and the accommodation space without preparing another dedicated member. Thus, even if the second path is clogged due to attachment of the liquid, it is possible to continue the use of the tank body and the cap by exchanging only a gasket.

For example, when the sealing member is a ring-shaped gasket, a hole penetrating through an outer perimeter surface and an inner perimeter surface of the gasket in a diameter direction can be used as a second path. Thus, a second path can be easily formed.

While any type of the aeration valve can be used in the present invention, a duckbill check valve is preferably used as an aeration valve.

The duckbill check valve is fabricated by integrally molding an elastic material. Therefore, compared with a check valve using a valve ball and a coil spring, the number of components can be reduced, and a mounting operation to the gas passage can be easier. In particular, when a hole penetrating through the outer perimeter surface and the inner perimeter surface of the ring-shaped gasket in a diameter direction is taken as a second path, only inserting the duckbill check valve into this hole can complete the operation of mounting the aeration valve. However, the present invention does not preclude the use of a check valve using a valve ball and a coil spring or other check valves.

In the present invention, preferably, the aeration valve at least partially projects from the second path toward the accommodation space.

If the entire aeration valve is accommodated in the second path, the liquid entering the second path is assumed to stay around the aeration valve and to be solidified with time. This inhibits the operation of the aeration valve or causes the aeration valve to be clogged. By contrast, if the aeration valve at least partially projects from the second path toward the accommodation space, the liquid around the projecting aeration valve is mobile compared with the one inside the second path, thereby preventing the liquid from staying around the aeration valve and being solidified.

In the present invention, preferably, the sealing member is held by the tank body and the aeration valve is placed so that a gas outflow end thereof is oriented toward a bottom of the tank body. Thus, when the cap is removed from the mouth part, inadvertent (unwitting) touch of the operator to the aeration valve can be prevented. Note that the sealing member may be held on a cap side.

In the present invention, a plurality of second paths and aeration valves are preferably provided in a circumferential direction of the tank body.

As described above, the first path is not formed by intent. Therefore, depending on manufacturing tolerances of the mouth part and the cap and the state of mounting of the cap on the mouth part (in the case of a screwed type, the state of fastening), the position and area of the first path may vary. Moreover, depending on manufacturing tolerances of the aeration valve and the state of mounting of the cap on the mouth part, a problem may occur in opening and closing of the aeration valve. Thus, when the number of second paths connecting to the first path is one, communicative connection between the first path and the second path and gas passage in the aeration valve may not be sufficiently ensured. This may occur not only from the start of use of the liquid tank but also in mid course of use. Therefore, by providing a plurality of second paths and aeration valves, even if one second path and one aeration valve do not function, the remaining second path and aeration valve are caused to function, thereby reliably performing aeration and securing outflow of the liquid from the accommodation space.

The liquid tank of the present invention described above can be used for a dental device including a liquid tank for accommodating a liquid to be supplied to a dental handpiece, a flow path for supplying the liquid flowing out from the liquid tank to the dental handpiece, and a pump discharging the liquid to the flow path toward the dental handpiece.

According to the present invention, a liquid tank capable of preventing a gas passage from being clogged is provided, and therefore no maintenance for preventing clogging is required or the frequency of maintenance can be significantly reduced.

DETAILED DESCRIPTION OF THE PREFERRED EMBODIMENTS

The present invention is described in detail below based on embodiments shown in the attached drawings.

First Embodiment

Figure 1:
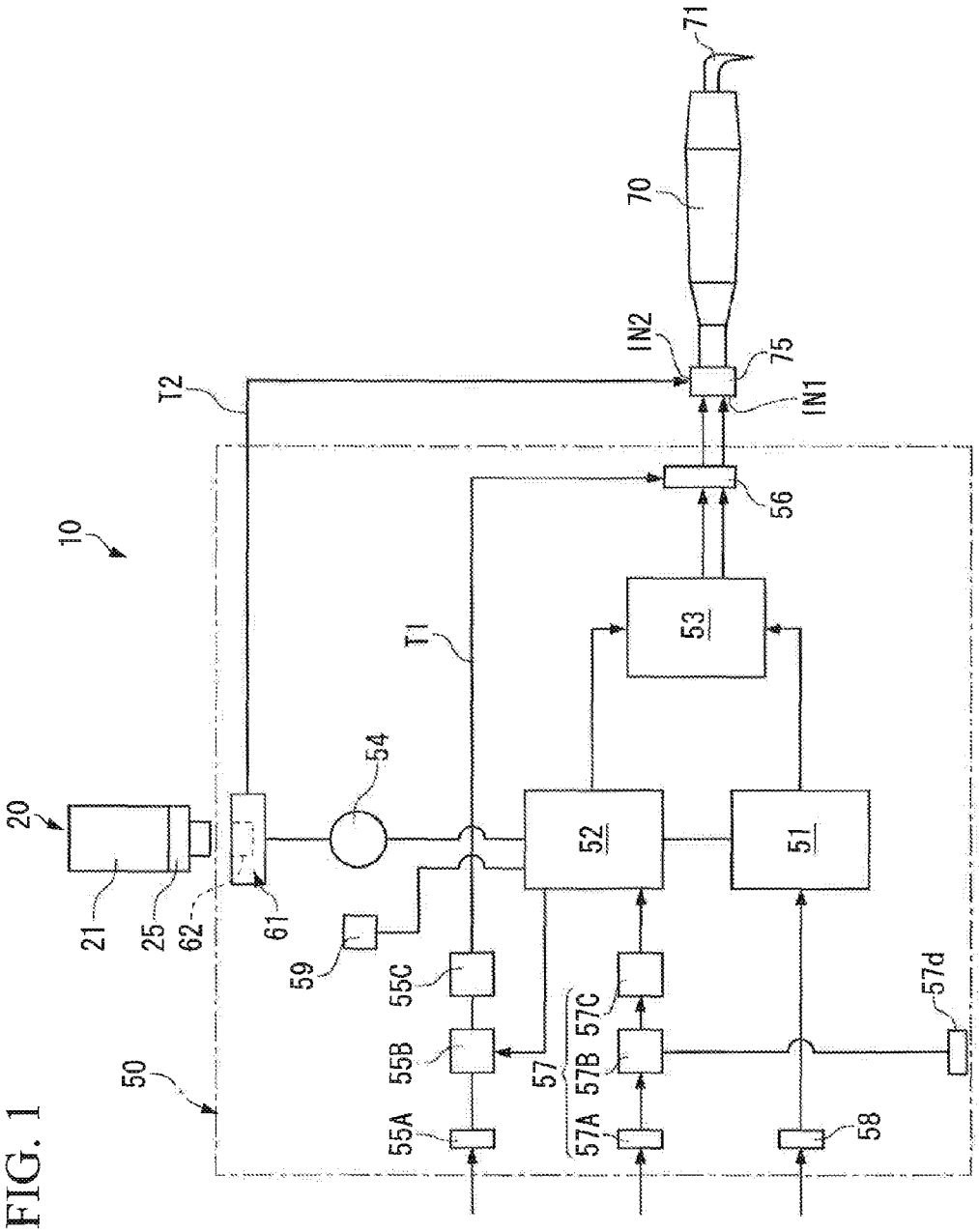
FIG. 1 is an entire schematic structural view of a dental device according to a first embodiment.

A dental device 10 shown in FIG. 1 has a liquid tank 20 for accommodating a liquid such as a chemical agent for use in dental treatment and a dental device body part 50 to which a dental handpiece 70 is connected via a connecting member (not shown) such as a tube containing a liquid passage, an electrical wiring, an optical fiber, and others.

The dental device body part 50 comprises main parts including a control board 51, a power supply and pump board 52, an oscillation board 53, a pump motor 54, and a water supply flow path T1, and others.

The control board 51 comprises an operation circuit for transmitting a signal from an operation button to a microcomputer circuit, the microcomputer circuit performing ON/OFF control over another circuit upon reception of signal from a foot switch via a terminal 58 and a signal from the operation circuit, and a display circuit for displaying an actuation conditions of this microcomputer circuit with LEDs or the like.

The power supply and pump board 52 comprises a pump control circuit for controlling the pump motor 54 upon reception of signals inputted from a motor-speed adjusting device 59 and the microcomputer circuit, an electromagnetic-valve control circuit for opening and closing an electromagnetic valve 55B upon reception of a signal inputted from the microcomputer circuit, and a main power supply circuit for supplying electricity to each circuit. An electrical path 57 to this main power supply circuit is to lead electricity from an AC inlet 57A via an open/close switch 57B and from a power supply transformer 57C to the main power supply circuit. The open/close switch 57B is turned ON/OFF by a power switch 57D, and the voltage of the inputted electricity is decreased by the power supply transformer 57C to a predetermined voltage.

The oscillation board 53 comprises a lamp power supply circuit for turning a lamp incorporated in the dental handpiece 70 ON/OFF and an ultrasonic oscillation circuit performing sweep oscillation to find a resonance point between an electrostrictive oscillator incorporated in the dental handpiece 70 and a tip chip 71 and, when finding a resonance point in a second cycle, locking at that resonance point. Signals from these lamp power supply circuit and the ultrasonic oscillation circuit are outputted via an output terminal 56.

The water supply flow path T1 is a path for supplying water such as tap water to the dental handpiece 70, and is provided so as to start from a terminal 55A for taking in water to continue to the output terminal 56 via the electromagnetic valve 55B and a water-amount adjusting valve 55C.

In the water supply flow path T1, when intake of water therefrom is selected, the electromagnetic-valve control circuit of the power supply and pump board 52 becomes active to cause the electromagnetic valve 55B to be opened or closed in conjunction with ON/OFF of the foot switch, thereby adjusting the water amount to an appropriate amount by the water-amount adjusting valve 55C. This water passes through the output terminal 56 and a relay connector 75 to be introduced to the dental handpiece 70, which has a tip provided with an injection nozzle from which the water is injected.

On the other hand, when intake of the liquid L such as a chemical agent accommodated in the liquid tank 20 is selected, the pump control circuit of the power supply and pump board 52 becomes active to cause the pump motor 54 to rotate or stop in conjunction with ON/OFF of the foot switch. By activating a roller squeezing a tube pump (both not shown), the pump motor 54 causes suction and discharge of the liquid L based on a change in pressure occurring in the tube. The liquid amount for suction (or for discharge) is adjusted by operating the motor-speed adjusting device 59 to cause the pump control circuit to increase and decrease the number of revolutions of the pump motor 54. The liquid L discharged from the tube pump is guided through a liquid supply flow path T2 (flow path) toward the relay connector 75 to be supplied to the dental handpiece 70. In this manner, when the liquid L accommodated in the liquid tank 20 is supplied to the dental handpiece 70, a negative pressure occurs inside of the liquid tank 20, as well known.

Note that a check valve is incorporated in each of a an input side IN1 of water such as tap water and a liquid input side IN2 from the liquid tank 20 in the relay connector 75, thereby preventing backflow of each liquid (water and the liquid L).

The dental device body part 50 comprises a liquid-tank placing part 61. In this liquid-tank placing part 61, a receiving part 62 for placing the liquid tank 20 is formed.

Figure 2:
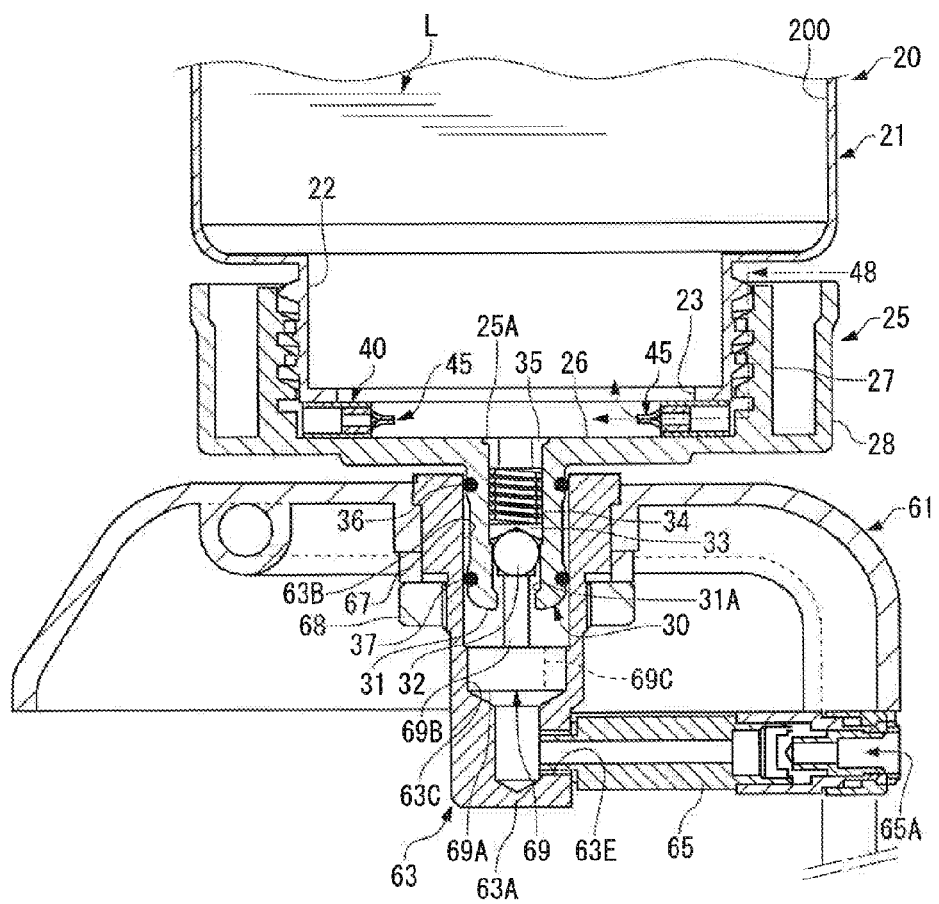
FIG. 2 is a sectional view of a liquid tank according to the first embodiment placed in a liquid-tank placing part.

As shown in FIG. 2, the receiving part 62 has an adaptor 63 and an opening member 69 as main structures.

As shown in FIG. 2, the adaptor 63 is held by the liquid-tank placing part 61 via a first fixing member 67 and a second fixing member 68.

The cylindrically-shaped adaptor 63 comprises a receiving cavity 63B receiving a valve accommodation body 31, which will be described further below. The receiving cavity 63B is a hole opening on an upper surface of the adaptor 63 and having a circular-shaped section formed in the course of reaching a bottom wall 63A a predetermined distance away from the upper surface. In an intermediate portion of this receiving cavity 63B in a vertical direction, a step part 63C having an inner diameter slightly smaller than that of an upper part is formed. Furthermore, the inner diameter below the step part 63C is further reduced. In the adaptor 63, a lateral hole 63E communicatively connecting to a lower end of the receiving cavity 63B and outside is bored in a diameter direction of the receiving cavity 63B. To this lateral hole 63E, a connecting tube 65 is coupled. To an opening 65A at an end of this connecting tube 65, a tube pump (not shown) is coupled.

When the liquid tank 20 is mounted on the liquid-tank placing part 61, the opening member 69 opens a liquid flow valve 30 by pushing a valve ball 32 of the liquid flow valve 30, which will be described further below, thereby allowing the liquid L to flow outside.

The opening member 69 includes a fixing part 69A having a large diameter and an acting part 69B having a small diameter and projecting from the fixing part 69A in an axial direction. In the fixing part 69A, notch parts 69C each in an arc shape in a planar view are equidistantly formed at three positions on an outer perimeter surface.

The opening member 69 is held in the receiving cavity 63B with the fixing part 69A being, for example, press-fitted. The fixing part 69A is positioned in the vertical (axial) direction by the step part 63C of the receiving cavity 63B. Notch parts 69C are formed on the outer perimeter surface of the fixing part 69A and the liquid L flows through the notch parts 69C. Therefore, the fixing part 69A placed in the receiving cavity 63B configures a liquid passage through which the liquid L flows.

As shown in FIG. 2, the liquid tank 20 includes a tank body 21 having an accommodation space 200 for accommodating the liquid L, a cap 25, the liquid flow valve 30 for controlling a flow of the liquid L in the accommodation space 200 toward the dental handpiece 70, a gasket 40 as a sealing member provided between the cap 25 and the tank body 21 (specifically, its mouth part 22), and an aeration valve 45 provided in the gasket 40.

The cylindrically-shaped tank body 21 includes a mouth part 22. The mouth part 22 has an opening 23. Through this opening 23, the liquid L flows in at the time of accommodating the liquid. At the time of mounting on the liquid-tank placing part 61, the liquid L flows out toward the dental handpiece 70. In an outer perimeter surface of the mouth part 22, screw threads 22A to be engaged with (screwed in) the cap 25 are formed. This tank body 21 is placed in the liquid-tank placing part 61 with the mouth part 22 oriented downward. Note that the tank body 21 is normally made of a resin material. The same goes for the cap 25.

By being mounted on the mouth part 22 of the tank body 21, the cap 25 closes the opening 23 of the mouth part 22.

Figure 4:
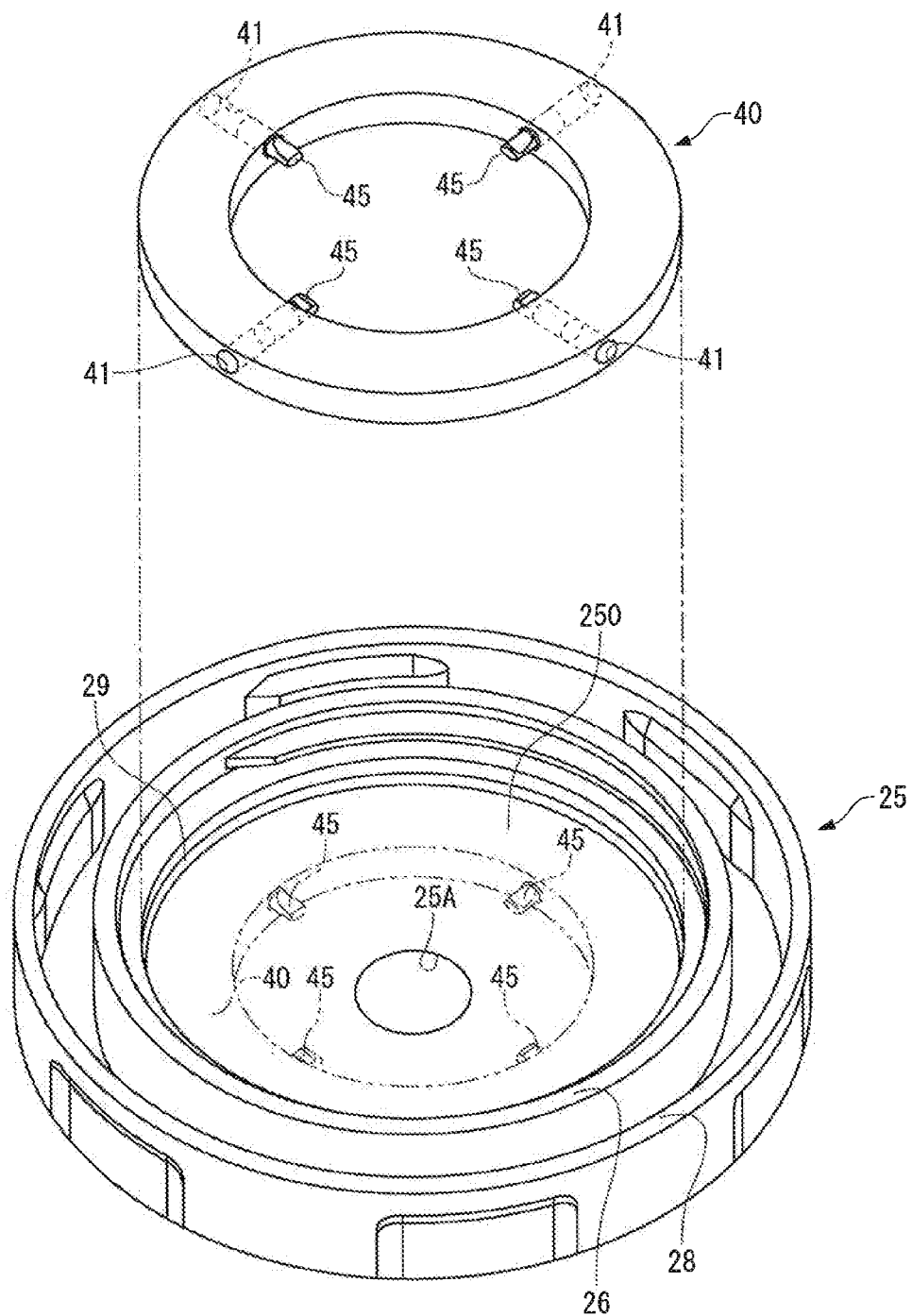
FIG. 4 is an exploded perspective view of a cap and a gasket.

As shown in FIG. 2 and FIG. 4, the cap 25 has a disk-shaped lid part 26 covering the opening 23 when mounted on the mouth part 22, a cylindrically-shaped mounting part 27 standing from a predetermined position near an outer perimeter of the lid part 26, and a gripping part 28 standing from the lid part 26 outside of the mounting part 27. On an inner perimeter surface of the mounting part 27, screw threads 27A to be engaged with the screw threads 22A of the mouth part 22 are formed.

The cap 25 is a cap of a screwed type in which mounting on and removal from the mouth part 22 (the tank body 21) is performed with the screw threads 27A and 22A engaged with each other. With the mouth part 22 and the mounting part 27 being stacked in their diameter direction, the cap 25 is mounted on the tank body 21.

The liquid flow valve 30 has the cylindrically-shaped valve accommodation body 31 standing from an outer edge part of a through hole 25A formed at the center of the lid part 26 toward a receiving part 62 side, the valve ball 32 placed inside the valve accommodation body 31, a holding part 33 holding the valve ball 32 from a base end side (a lid part 26 side) of the valve accommodation body 31, a coil spring 34 pushing the holding part 33 toward a tip side of the valve accommodation body 31, and an engaging member 35 engaging an end opposite to a valve ball 32 side of the coil spring 34 with an inner wall of the through hole 25A. On a tip inner wall of the valve accommodation body 31, a tapered surface (a valve seat) 31A is formed to receive the valve ball 32 pressured by the coil spring 34.

In a state where the liquid tank 20 is removed from the liquid-tank placing part 61 (refer to FIG. 6), the valve ball 32 is pressed onto the tapered surface 31A to close the liquid flow valve 30, thereby inhibiting outflow of the liquid L in the accommodation space 200 to outside.

As shown in FIG. 2, in the state in which the liquid tank 20 is placed in the liquid-tank placing part 61, the acting part 69B of the opening member 69 is against a pressing force of the coil spring 34 to separate the valve ball 32 from the tapered surface 31A. Therefore, the liquid flow valve 30 is opened so as to allow outflow of the liquid L to outside.

Then, the liquid L is supplied to the tube pump (not shown) via the through hole 25A, the inside of the valve accommodation body 31, the receiving cavity 63B of the adaptor 63, and the connecting tube 65.

Also, when the liquid tank 20 is placed in the liquid-tank placing part 61, the valve accommodation body 31 is inserted into the receiving cavity 63B of the adaptor 63. On an outer perimeter of the valve accommodation body 31, O rings 36 and 27 are placed, thereby preventing the liquid L in the receiving cavity 63B of the adaptor 63 from leaking to the outside.

This valve accommodation body 31 also functions as a coupling part of the liquid tank 20 and the liquid-tank placing part 61. Alternatively, as a separate body from the valve accommodation body 31, a coupling part of the liquid tank 20 and the liquid-tank placing part 61 may be provided.

Also, while the valve accommodation body 31 is integrally provided to the cap 25, the valve accommodation body 31 may be configured as a separate body, and the liquid flow valve 30 can be a cartridge removable from the cap 25. The valve accommodation body 31 of this cartridge type is mounted on the cap 25 so that the inside communicatively connects to the through hole 25A of the lid part 26.

Figure 3:
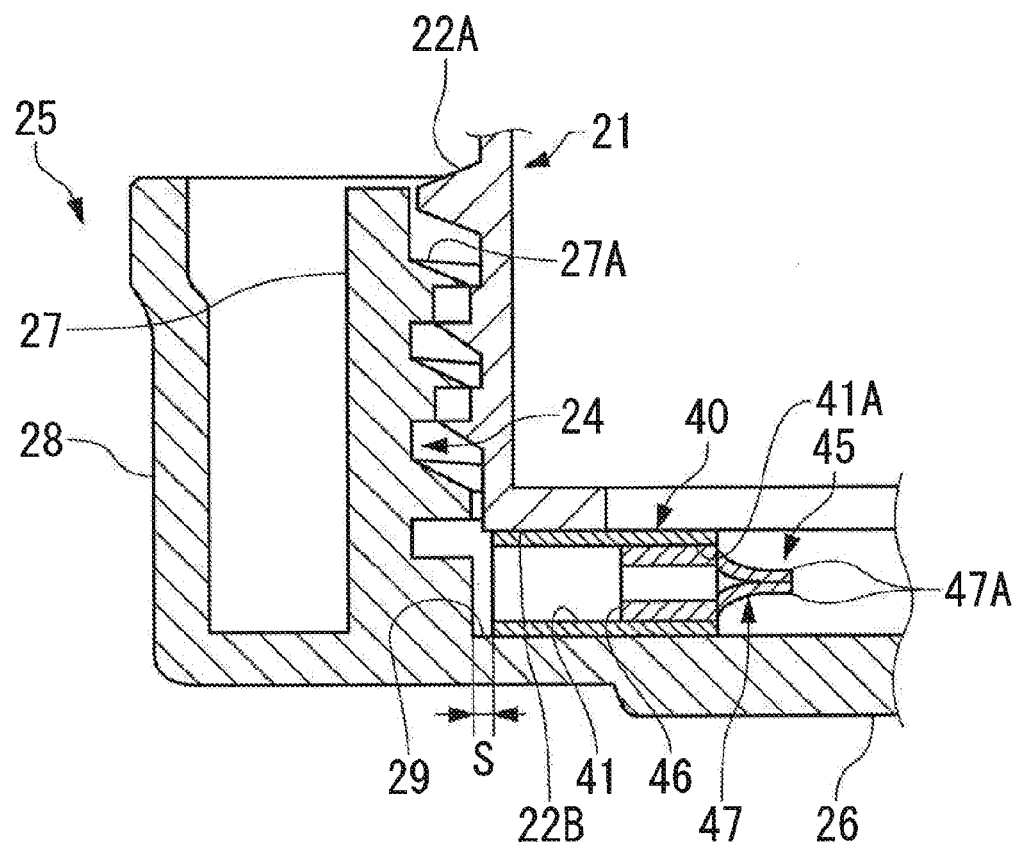
FIG. 3 is a partially enlarged view of FIG. 2.

As shown in FIG. 3, with the screw treads 27A of the mounting part 27 engaged with the screw treads 22A of the mouth part 22, the cap 25 is mounted on the tank body 21. The screw treads 22A and the screw treads 27A are in contact with each other in their longitudinal direction, that is, approximately along the circumferential direction (along a spiral direction) of the mouth part 22 and the mounting part 27. Thus, since air (gas) passes through a space between the mouth part 22 and the mounting part 27, it is understood that a fine gap 24 occurs therebetween partially or entirely in the circumferential direction. In the present embodiment, this gap 24 is used as a gas passage (a first path) for aeration.

Note that while the method of mounting the cap 25 on the tank body 21 is a screwed type in the preset embodiment, the screwed type is merely an example of a technique of mounting the cap 25, and an appropriate cap mounting technique in which the gap 24 occurs between the cap 25 and the tank body 21 can be adopted.

Figure 5A:
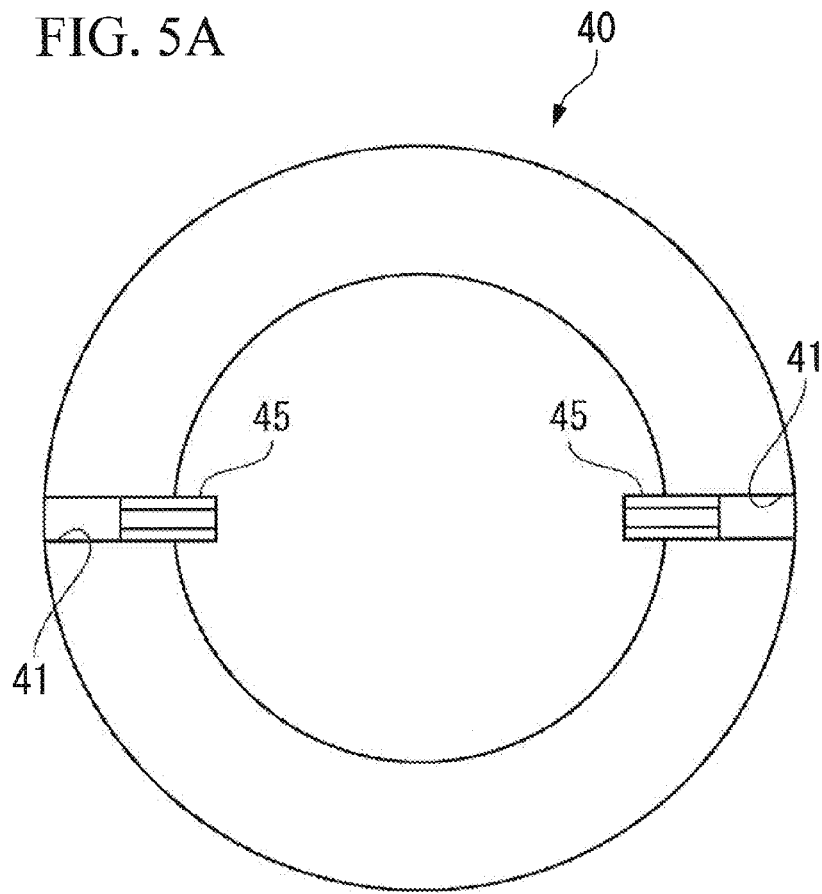
FIG. 5A is a cross section view of an aeration valve and a gasket.
Figure 5B:
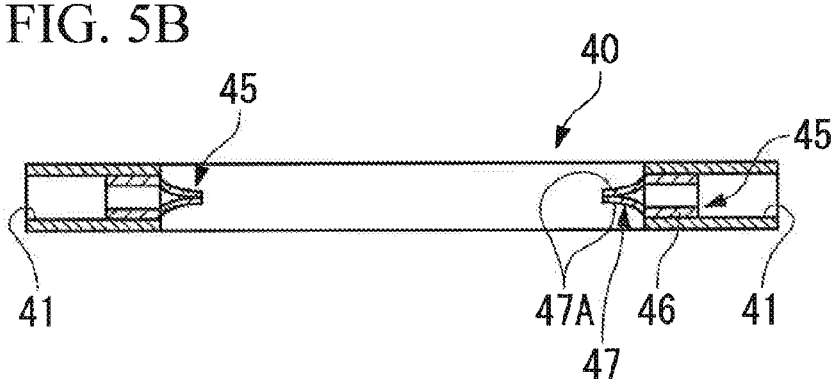
FIG. 5B is a longitudinal section view of the aeration valve and the gasket.

As shown in FIG. 4 and FIG. 5A, the gasket 40 is an annular-shaped member. In the gasket 40, paths 41 are formed penetrating through the gasket 40 along a diameter direction. While an example is shown in the present embodiment in which the paths 41 penetrate through along the diameter direction of the gasket 40, the paths 41 are not restricted to those along the diameter direction as long as they penetrate through along a direction connecting an inner perimeter and an outer perimeter of the gasket 40, and the paths 41 along a direction inclined with respect to the diameter direction can be formed. Also, while four paths 41 are equidistantly formed in the circumferential direction of the gasket 40 in the present embodiment, the number of paths 41 is not restrictive and, for example, only one path 41 may be formed. This path 41 corresponds to a second path in the present invention. Note that if a resin material is subjected to injection molding to fabricate the gasket 40, the paths 41 and the gasket 40 can be integrally formed.

On each of the paths 41, an aeration valve 45 is provided. The aeration valve 45 is positioned on an inner perimeter side of the gasket 40, and part of the aeration valve 45 is provided so as to project from an opening 41A on the inner perimeter side of the gasket 40 toward the center of the gasket 40. More specific description is made below.

As shown in FIG. 3, the aeration valve 45 is a one-way valve, which is a so-called duckbill check valve, including a hollow body part 46 and a valve body 47 continuous to one end of the body part 46. The valve body 47 includes paired beaked parts 47A with their tips pressed toward each other, and is configured of a rubber-made, integrally-molded product.

The body part 46 of the aeration valve 45 is held by the gasket 40 in the path 41. On the other hand, the entire valve body 47 projects from the opening 41A of the gasket 40.

This aeration valve 45 lets air (gas) flow out from outside of the liquid tank 20 toward the inside, and prevents the liquid L in the accommodation space 200 from flowing through the path 41 toward outside. That is, in the aeration valve 45, gas flows out from a tip (a gas outflow end) of the valve body 47.

As shown in FIG. 3 and FIG. 4, the gasket 40 described above is placed in a recessed part 29 formed by the lid part 26 of the cap 25 and the mounting part 27. Between a side surface on the outer perimeter side of the gasket 40 and the mounting part 27, as shown in FIG. 3, a slight gap S (configuring a second path together with the path 41) is formed.

When the cap 25 is mounted on the mouth part 22, as shown in FIG. 3, the gasket 40 is positioned between an end face 22B of the mouth part 22 and the lid part 26 of the cap 25 and is in close contact with the end face 22B and the lid part 26. Thus, the space between the cap 25 and the mouth part 22 is sealed, thereby preventing the liquid L from leaking to the outside of the liquid tank 20.

Here, with the gasket 40 being interposed between the cap 25 and the mouth part 22, the gap 24 between the cap 25 and the mouth part 22 and the path 41 communicatively connect to each other via the gap S. That is, while sealing the space between the end face 22B of the mouth part 22 and the lid part 26, the gasket 40 lets gas taken from outside and passing through the gap 24 flow into the accommodation space 200 with the presence of the path 41. As such, the liquid tank 20 includes a gas passage 48 (shown in FIG. 2) including the gap 24 (a first path) and the path 41 (a second path) communicatively connecting to the gap 24 and the accommodation space 200.

Meanwhile, when the liquid tank 20 is mounted on the liquid-tank placing part 61, the acting part 69B of the opening member 69 pushes the valve ball 32 to open the liquid flow valve 30. In this state, when the foot switch is turned ON, the pump motor 54 is activated and the liquid L in the liquid tank 20 passes through the liquid flow valve 30 to be supplied to the dental handpiece 70. Then, a negative pressure occurs in the accommodation space 200. However, since outer air passes through the gas passage 48 to be taken in the accommodation space 200, the negative pressure in the accommodation space 200 is compensated for. Thus, supply of the liquid L to the dental device body part 50 continues without stopping.

In the dental device 10 of the present embodiment described above, the gap 24 inevitably formed between the cap 25 and the mouth part 22 is used as the gas passage 48. Since the gap 24 between the mouth part 22 and the cap 25 (its mounting part 27) is subtle, dust is difficult to enter this gap 24. Even if dust enters, the gap 24 is present in the circumferential direction of the mouth part 22 and the mounting part 27 over a wide range, and thus only a part of the gap 24 is possibly clogged with dust. Therefore, there is no possibility that the gas passage 48 is clogged with dust.

In addition, if the cap 25 is removed from the mouth part 22 of the tank body 21, the inner perimeter surface of the mounting part 27 and the outer perimeter surface of the mouth part 22 can be cleaned. That is, dust in the gas passage 48 (the gap 24) formed between the mounting part 27 and the mouth part 22 can be easily removed.

Also, since the path 41 configuring part of the gas passage 48 is formed in the gasket 40 generally used for sealing a space between the cap 25 and the tank body 21, a separate member is not required for forming a portion of the gas passage 48 corresponding to the path 41. Furthermore, since this gasket 40 is used to seal the space between the cap 25 and the mouth part 22, only the subtle gap S is enough as a distance between the gap 24 and the path 41 of the gasket 40 in a gas flowing direction. This gap S can also be formed without preparing any separate member. In view of these points, in addition to using the gap 24 as the gas passage 48 as described above, the present embodiment is advantageous in reducing the number of components. However, this gap S is not an indispensable element for the present invention.

Furthermore, since the path 41 and the aeration valve 45 are provided in the gasket 40, when the path 41 and the aeration valve 45 are clogged, only the gasket 40 can be replaced to continue the use of the liquid tank 20.

Figure 8:
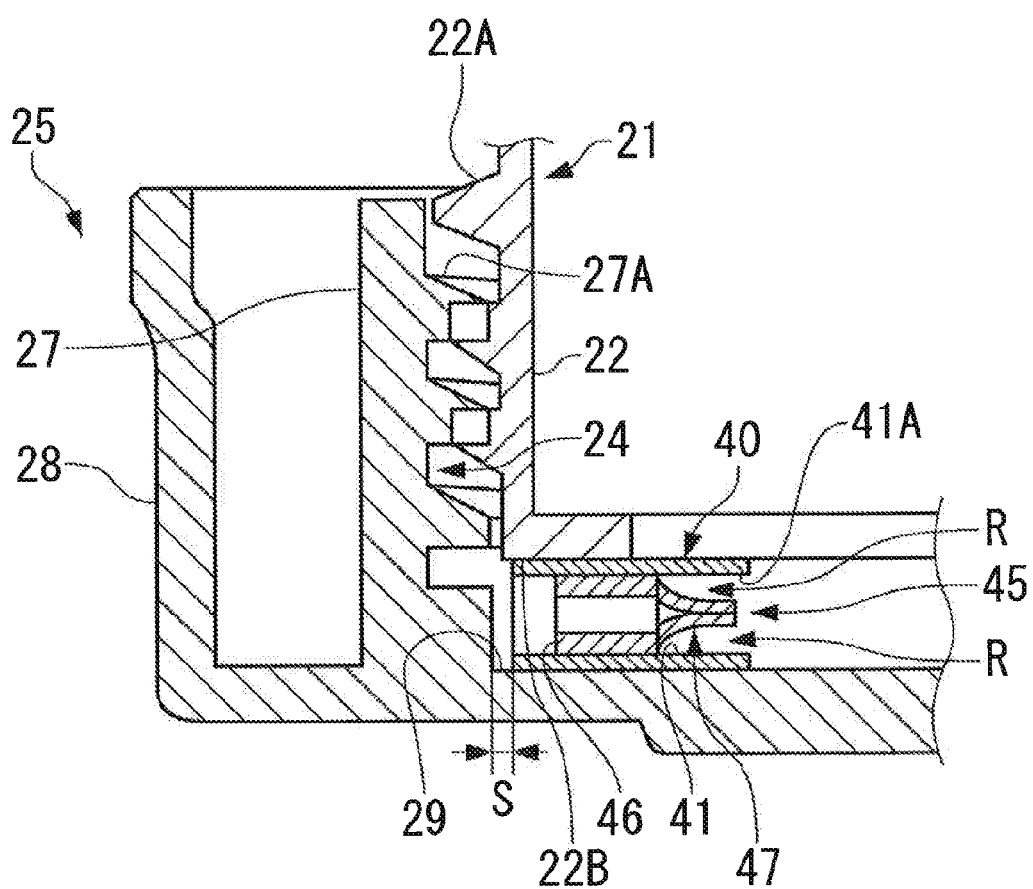
FIG. 8 is a partially enlarged view of a modification example of the first embodiment.

Still further, since the valve body 47 of the aeration valve 45, that is, the gas outflow end, projects from the opening 41A on the inner perimeter side of the gasket 40 toward the accommodation space 200, the liquid L is less prone to stay around the valve body 47. That is, as shown in FIG. 8, if the valve body 47 in addition to the body part 46 is placed inside of the path 41, a gap R is formed between the valve body 47 and the wall surface of the gasket 40 forming the path 41. After entering this gap R, the liquid L stays and is solidified around the valve body 47, thereby possibly inhibiting discharge of gas from the valve body 47. By contrast, as in the present embodiment, if the valve body 47 projects from the opening 41A on the inner perimeter side of the gasket 40, no gap R in which the liquid L stays is formed, thereby preventing the liquid L from being solidified around the valve body 47.

Still further, the number of components of the duckbill check valves for use as the aeration valve 45 is small and its structure is simple, compared with a check valve using a valve ball and a coil spring. Also, since the aeration valve 45 is an integrally-formed member, it can be easily mounted on a narrow place such as the path 41 of the gasket 40. Therefore, this is advantageous in reducing cost of the liquid tank 20 by reducing the number of components and the number of manufacturing processes. The aeration valve 45, which is a duckbill check valve herein, is sensitive even to a slight pressure difference. Therefore, by reliably compensating for the negative pressure in the tank body 21, the liquid L can be supplied to the dental handpiece 70 without interruption. With this, reliability of the dental device 10 can be improved.

In the present embodiment, the paths 41 and the aeration valves 45 are provided at four points in the circumferential direction of the mouth part 22, thereby more reliably compensating for the negative pressure. That is, due to the fastening state between the cap 25 and the mouth part 22, manufacturing tolerances of the aeration valve 45, and others, the position and area where the gap 24 occurs may vary, and a problem may occur in opening and closing of the aeration valve 45. However, by providing the paths 41 and the aeration valves 45 at four points in the circumferential direction, outer air can be reliably taken in the accommodation space 200 via the gap 24, the path 41, and the aeration valve 45.

Second Embodiment

A second embodiment includes a structure similar to that of the first embodiment except the structure of a gasket 80. Therefore, the gasket 80, which is a different point from the first embodiment, is mainly described below.

Figure 6:
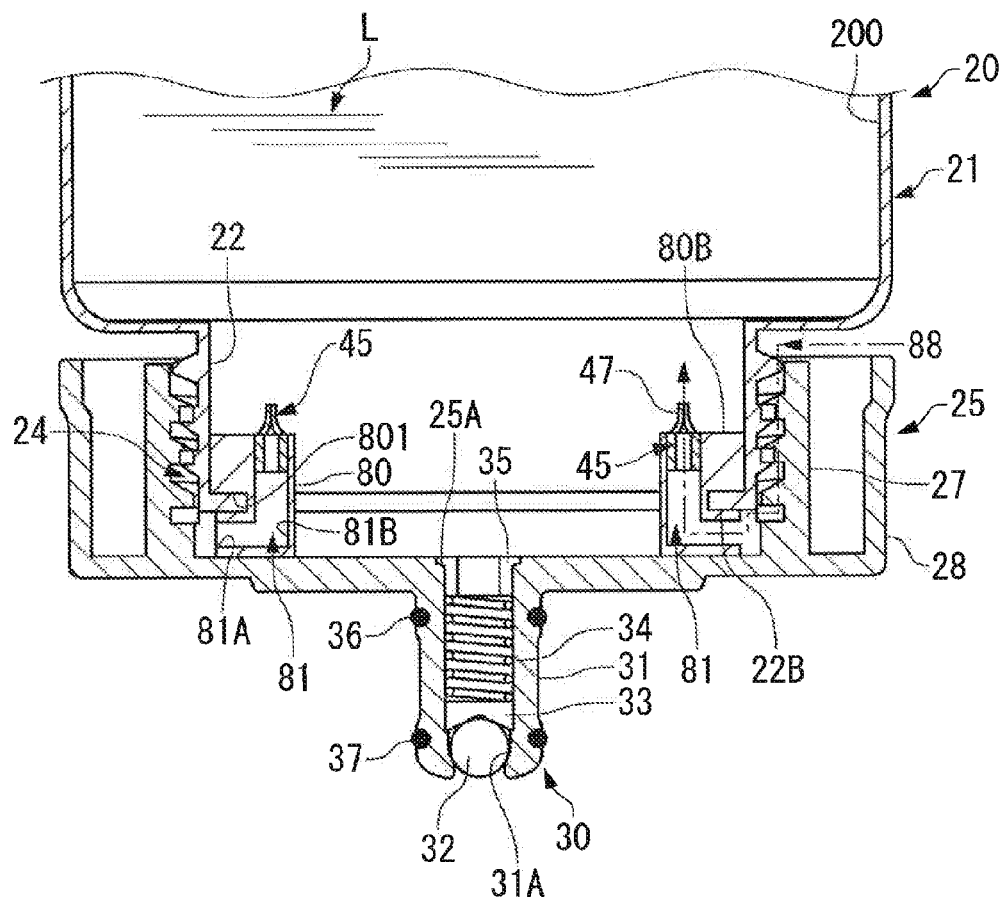
FIG. 6 is a sectional view of a liquid tank according to a second embodiment.
Figure 7:
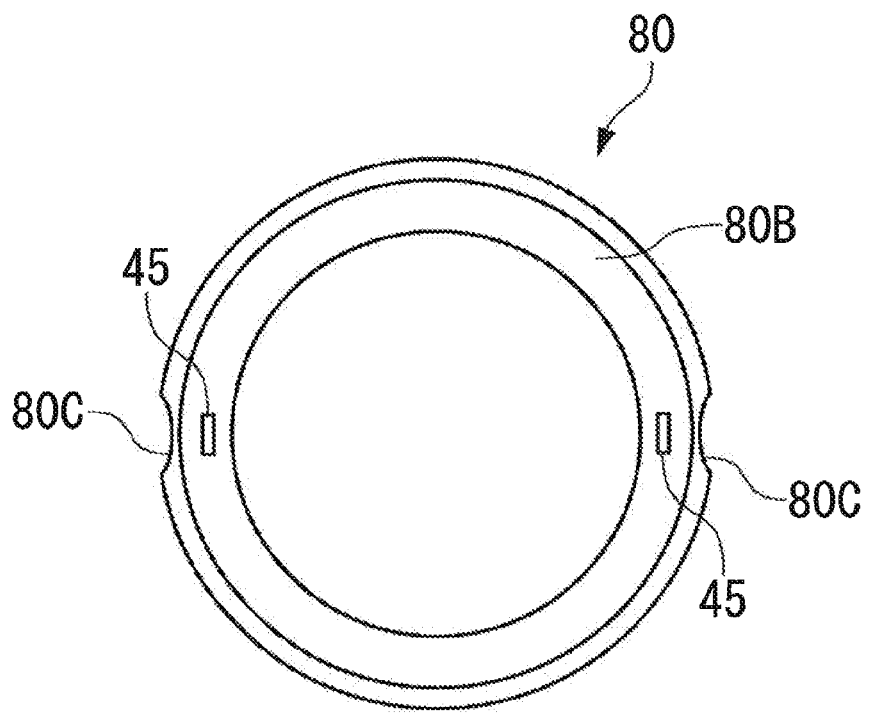
FIG. 7 is a plan view of a gasket and an aeration valve of the second embodiment.

As shown in FIG. 6 and FIG. 7, a gasket 80 according to the second embodiment of the present invention is in the form of a cylindrical shape, and has a holding groove 801 continuing in a circumferential direction at an intermediate part in a height direction. With the end face 22B part of the mouth part 22 being inserted into the holding groove 801, the gasket 80 is held by the mouth part 22.

In the gasket 80, two paths 81 communicatively connecting to the gap 24 and the accommodation space 200 are equidistantly formed in the circumferential direction. As with the first embodiment, the number of paths 81 is not restrictive. In the present embodiment, a gas passage 88 including the gap 24 and the path 81 is provided.

The path 81 includes a diameter-direction path 81A and an axial-direction path 81B, and is bent at a boundary therebetween.

The diameter-direction path 81A has one end opening to a notch 80C (FIG. 7) formed on an outer perimeter surface of the gasket 80, and is formed in a diameter direction to the other end positioned outside of the inner perimeter surface of the gasket 80 in the diameter direction. Since the notch 80C is formed, air permeability between the gap 24 and the path 81 is ensured.

The axial-direction path 81B has one end coupling to the other end of the diameter-direction path 81A and the other end opening to an upper surface 80B.

In the axial-direction path 81B, the aeration valve 45 is provided. As with the first embodiment, the aeration valve 45 has the body part 46 held by the gasket 80 in the axial-direction path 81B. The valve body 47 of the aeration valve 45 projects from the upper surface 80B of the gasket 80 toward the bottom (a portion facing the opening 23 in the tank body 21) of the tank body 21.

According to the present embodiment, in addition to effects similar to those of the first embodiment, the following effects can be achieved. That is, the gasket 80 is held by the mouth part 22 and the aeration valve 45 is placed toward the bottom of the tank body 21. Thus, when the cap 25 is removed, the operator can be prevented from inadvertently touching the aeration valve 45. Thus, it is possible to prevent the aeration valve 45 from being damaged and from becoming dirty.

While the embodiments of the present invention have been described, other than the above, the configurations cited in the above described embodiments can be selected or omitted, or can be arbitrarily changed to the other configurations, without departing from the gist of the present invention.

For example, the path 41 (the second path) is not restricted to be formed in the gaskets 40 and 80, but can also be formed in the tank body 21, the cap 25, or a boundary portion between the tank body 21 and the cap 25.

Furthermore, while the duckbill check valve is exemplarily shown as the aeration valve, a porous film letting gas to pass through but restricting passage of liquid can be used as the aeration valve. This porous film is made of a material including fine pores in hundreds of millions per square centimeter, and may be called a waterproof vapor-permeable film.

What is claimed is:

1. A dental device comprising:
a liquid tank having an accommodation space for accommodating a liquid to be supplied to a dental handpiece;
a flow path for supplying the liquid flowing out from the liquid tank to the dental handpiece; and
a pump discharging the liquid to the flow path toward the dental handpiece, the liquid tank comprising a tank body having a mouth part with an opening for inflow and outflow of the liquid;

a cap mounted on the mouth part, the cap comprising a lid part extending across the opening to close the opening, the interior surface of the cap cooperates with a compatible exterior portion of the mouth part to couple the cap to the liquid tank;

a liquid passage formed in the lid part through which the liquid in the liquid tank flows toward outside;

a gas passage having a first path between an outer perimeter surface of the mouth part and a mounting part of the cap, the first path communicatively connecting to outside and a second path communicatively connecting to the first path and the accommodation space;

a liquid flow valve provided on the lid part in the liquid passage to allow or inhibit a flow of the liquid to outside; and an aeration valve provided on the gas passage to compensate for a negative pressure occurring in the accommodation space.

2. The dental device according to claim 1, further comprising a sealing member sealing a space between the mouth part and the cap, wherein
the second path is at least partially formed in the sealing member.

3. The dental device according to claim 2, wherein
the sealing member is held by the tank body, and
the aeration valve is placed so that a gas outflow end thereof is oriented toward a bottom of the tank body.

4. The dental handpiece according to claim 2, wherein the sealing member is a gasket.

5. The dental device according to claim 1, wherein
the aeration valve is a duckbill check valve.

6. The dental device according to claim 5, wherein
the aeration valve at least partially projects from the second path toward the accommodation space.

7. The dental device according to claim 1, wherein a plurality of said second paths and said aeration valves are provided in a circumferential direction of the tank body.

8. The dental device according to claim 1, wherein screw threads formed in an outer surface of the mouth part are configured to screw into mating screw threads formed in an inner surface of the cap.

9. The dental handpiece according to claim 1, wherein the aeration valve is provided between the mouth part and the cap on the gas passage and communicatively connects the accommodation space and the outside.

* * * * *